United States Patent [19]

Stoy et al.

[11] Patent Number: 4,563,182
[45] Date of Patent: Jan. 7, 1986

[54] RECTAL INSERT

[75] Inventors: Vladimir A. Stoy; George P. Stoy, both of Princeton, N.J.

[73] Assignee: Health Products Research, Inc., Somerville, N.J.

[21] Appl. No.: 667,265

[22] PCT Filed: Mar. 4, 1983

[86] PCT No.: PCT/US83/00300
§ 371 Date: Nov. 1, 1984
§ 102(e) Date: Nov. 1, 1984

[87] PCT Pub. No.: WO84/03434
PCT Pub. Date: Sep. 13, 1984

[51] Int. Cl.⁴ .............................................. A61M 31/00
[52] U.S. Cl. .................................... 604/285; 128/401; 424/DIG. 15
[58] Field of Search ............... 604/285, 287, 288, 290, 604/291; 128/401, 341, 343; 424/19, DIG. 15

[56] References Cited

U.S. PATENT DOCUMENTS

| | | | |
|---|---|---|---|
| 3,826,242 | 7/1974 | Eggers | 128/341 |
| 3,894,539 | 7/1975 | Tallent | 128/341 |
| 3,939,842 | 2/1976 | Harris | 128/401 |

Primary Examiner—John D. Yasko
Attorney, Agent, or Firm—Omri M. Behr

[57] ABSTRACT

A method of treating hemorrhoids which comprises inserting into the rectum of a subject afflicted therewith a substantially cylindrical shaped insert, comprising a water swellable polymer having a water content of at least 35% by weight, said insert having previously been frozen by being subjected to a temperature below 0° C. for a sufficient amount of time to freeze the free water therein and maintaining said insert with at least a portion thereof outside the sphincter muscle, and apparatus therefore.

16 Claims, 8 Drawing Figures

RECTAL INSERT

BACKGROUND OF THE INVENTION

The hemorrhoids, or piles, are swollen varicose veins in the mucous membrane inside or just outside the rectum.

One common cause of piles is constipation and the straining to eliminate hard, dry stool. The excessive pressure causes a fold of the membraneous rectal lining to slip down, thus pinching the veins and irritating them.

Women during pregnancies are particularly subject to the hemorroidal problem because of the pressure in the veins in the lower body area.

Other causes are diseases of the digestive tract resulting in anal infection, and cirrhosis of the liver, which obstructs blood flow and puts increased pressure on the hemorrhoidal veins.

Once the hemorrhoids are formed, they can further deteriorate or rupture by additional pressure during constipation and straining at stool, or by external pressure by long sitting (particularly if the piles are prolapsed or external).

The ruptured and bleeding piles are sensitive to infection; the swelling caused by inflamation affects, in turn, the hemorrhoids by pressing the veins.

The hemorrhoidal problems are self-accelerating and the prevention of the progressive deterioration of the problem is the essential condition of a successful treatment.

The treatment methods range from warm bath through ointments and suppositories to surgery or an injection chemotherapy to control bleeding and to eliminate the varicose veins. Often several methods are combined to address various aspects of the disease.

One approach to the treatment is to relieve the pain and to diminish the swelling by cooling of the hemorrhoidal tissue. For instance Cowie in U.S. Pat. No. 969,134 suggested the use of hollow insert filled with crushed ice or another cooling medium which was refilled for every use.

More recently Harris in U.S. Pat. No. 3,939,842 suggested a plastic rectal insert with encapsulated freezable liquid, preferrably water, equipped with a bulbous collapsible end. Both devices above have several shortcomings in common:

(1) The surface of the device may have very low temperature so that it can cause frost-bites to the sensitive rectal tissue. The frost-bites occur when the intracellular liquid is frozen, rupturing the cell membrane. This may happen even at moderately sub-zero temperatures if the contact between device and tissue is intimate and heat transfer efficient, which is the case for both devices.

(2) Neither of the devices is inherently disposable which can increase the risk of infection. Although the Harris device is intended to be disposable, it lacks any features preventing its multiple use. Its presumably higher cost, if compared with ointments or suppositories, may encourage its multiple use.

(3) Both devices have one single function, the cooling of the tissue in the rectal canal. This treatment has to be combined with other means, such as ointments, lubricants or suppositories etc., which support the treatment and the discomfort relief by delivering certain drugs, protective and lubricating layer onto the swollen tissue and by eventual softening the stool.

(4) Neither device can be applied without a lubricant.

Therefore, the freezable liquid encapsulated in a solid shell cannot utilize fully the beneficial cooling effect and introduces certain risks.

Suppositories cannot be used for the cooling effect because of their shape: the pressure of the sphincter squeezes them immediately from the rectal canal to bottom of the colon. This holds even for hydrogel suppositories, as described e.g. by Byrne and Aylott in U.S. Pat. No. 4,292,300, which could have otherwise sufficient heat capacity due to relatively high water content. The role of suppositories in general is drug delivery, and their cooling effect in the rectal canal was never suggested or anticipated. Therefore, suppositories in general differ substantially from the rectal inserts described either in the prior art or in the present invention.

SUMMARY OF THE INVENTION

It has been found that the free water in a hydrogel containing more than 35% by weight of water can be readily frozen by reducing the temperature of its environment approximately below 0° C., preferably below −5° C. It has further been found that such a frozen rigid body has the interesting property that as soon as its surface is contacted with skin at or close to body heat a substantially non-frozen gel film is immediately formed between the skin and the frozen portion of the gel. This useful property may be utilized in the treatment of hemorrhoids with or without the contemporaneous delivery of pharmaceutically active materials into the mucosa of the rectum.

The present invention provides a rectal insert made of frozen hydrogel, a method of making same and a method of using the same.

In its simplest form the invention comprises a substantially cylindrical insert of frozen hydrogel having a substantially conical nose portion for insertion into the rectum and a collar of substantially greater diameter than the main portion of the insert placed proximate to the rear end of the insert, said collar acting as a block to insertion of the device entirely through the sphincter muscle. This property permits application of reduced temperature to most of the areas liable to be effected by hemorrhoids.

Numerous different embodiments of this invention are discussed in further detail hereinbelow including especially means for permitting the device to be held in position by the sphincter muscle itself after insertion and not expelled as would be the natural tendency of action of said sphincter muscle and its adjacent musculature.

The device is provided in the form of a disposable "bubble type" package wherein the hydrogel is provided in gel form to the space provided by the bubble which is in the shape of the desired form of the rectal insert.

Prior to use the entire package is cooled, suitably by placing it in the freezer compartment of a domestic freezer. The package is then opened whereby, in the preferred embodiment the two halves of the bubble pack are separated to provide the frozen insert. The insert is then removed and inserted into the rectum of the afflicted subject. Where the simplest embodiment of the invention is utilized the muscle system of the rectum will tend to expel the insert unless the subject, after insertion, lies substantially flat on his stomach which would permit him to retain the device in place. The choice of the male pronoun is deliberate and not accidental since it has been found, surprisingly, that while male test subjects are not able to retain the insert in a sitting position, i.e. on a toilet, female test subjects have been able to do so without great difficulty.

The preferred embodiment having a further substantially frustro-conically shaped forward collar may be inserted while the subject is in the sitting position and will be retained because of the interaction of the rearward portion of the said collar with the internal face of the sphincter muscle.

The device is left in place for between 1 to 5 minutes after which time it may either be removed, or left in place until the combined action of body heat and pressure of the sphincter muscle dissolves that portion of the insert upon which it acts causing any undissolved portion of the insert, internal of the sphincter muscle to be retained and permitted to move up into the colon.

The hydrogels themselves which are utilized in the formation of the rectal insertions of the present invention are entirely without physiological effect and the thus produced gels, sols, or solutions thereof may be retained in the colon until the next bowel movement without any adverse physiological effect.

DESCRIPTION OF THE PREFERRED EMBODIMENTS

Figure 1:
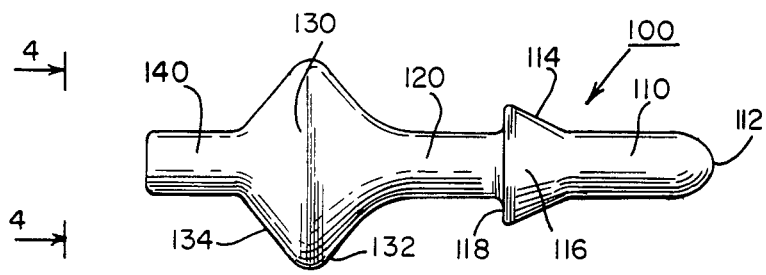
FIG. 1 is a plan view of the preferred embodiment of the rectal insert of the present invention.

The rectal insert of the present invention is preferably, but not solely, to be marketed as a blister type package having a blister of predetermined form in the form of the rectal insert itself, said blister being filled with a gel comprising a hydrogel polymer and water in proportions more particularly described hereinbelow.

The type of blister pack chosen will depend upon commercial considerations as well as the nature of the gel chosen. Gels having a water content of, say, 35-90% can be fairly shape sustaining and can be packed in packages having very little mold forming effect. Above 90% water the gels, at ambient temperature, are not form retaining. These gels can be retained either in a preformed substantially rigid blister pack made of, say, PVC or polystyrene. Alternately, "soft" blister packs of polyethylene may be used into which the gel is injected under moderate pressure, if desired by softening the pack with heat.

Prior to use the package is cooled below the freezing point of water. A temperature reduction to $-5°$ C. is generally suitable though any domestic freezer, which has temperatures down to about $-15°$ C. may also be employed.

It is an special advantage of the present invention that such further reduction in temperature carries no adverse effect such as frostbite during use.

This advantage arise from the special properties of water swellable polymers suitably hydrogels. When ice is contacted with a warm surface, such as skin, the top surface is melted to water which on application of pressure as will occur in the rectum, will be pushed away permitting the skin to contact the ice itself thus giving rise to frostbite. In contrast when a gel is frozen there is a phase separation of ice and gel. When the upper layer of ice is melted the water thus liberated remains in the gel, forming a layer whose temperature will not fall below $0°$ C. and at the same time prevents contact with the inner frozen surface. While the rectal insert could be either fluid or self form sustaining at ambient temperatures, the discussions which follow are directed to a description thereof in the frozen form.

In the use of the rectal insert in the treatment of hemorrhoids, (to which use the device is by no means limited as will be discussed in further detail hereinbelow) it is important to maintain contact between the cooling surface and the hemorrhoidal tissue for as long a period of time as possible. It has generally been accepted in the art that a minimum treatment time of 1 minute is essential while it would be desirable to increase the contact time up to approximately 5 minutes or more.

It is an important consideration in this treatment that hemorrhoidal veins occur in the area of the rectum itself in and around the sphincter muscle and outside the sphincter muscle. A successful device must therefore maintain contact in all areas. Thus, a device shaped in the form of a conventional suppository which will readily travel through the sphincter muscle and then up into the colon while satisfactory for chemical treatments of hemorrhoids is unsatisfactory for thermal treatment as the contact time is too short.

Figure 5:
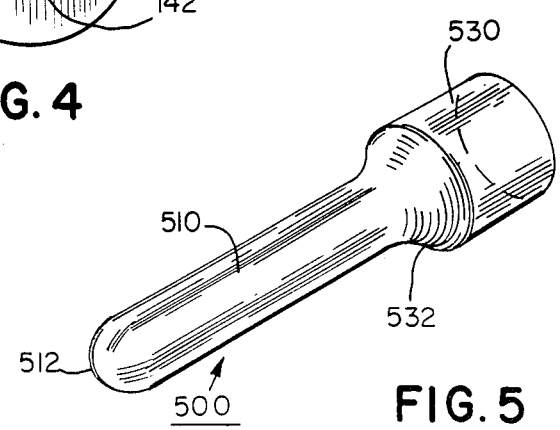
FIG. 5 is a simple embodiment of the rectal insert of the present invention.

The simplest device is illustrated as insert 500 in FIG. 5. Rectal insert 500 comprises a substantially cylindrical central shaft portion 510 having a substantially conical nose portion 512 and a stopper portion 530 having a forward surface 532. The device is used by inserting nose section 512 through the sphincter muscle of the rectum up to the point where surface 532 contacts the outside of said sphincter muscle. The insert is left in place until either it melts completely or is removed after a sufficient length of time has passed.

The general pressures generated by the sphincter muscle and adjacent muscles of the rectum when the subject is in the seated position tend to expel all inserted bodies. Thus, where the embodiment of FIG. 5 is employed it would be necessary to maintain constant inward pressure on the device which may be considered inconvenient and somewhat unesthetic. Alternatively, the device maybe readily inserted and maintained in position when the subject is lying face down on a bed. Even in this situation there are esthetic disadvantages because of the neccessity of protecting the bed against the melting insert by towels and the like. Nevertheless, despite the foregoing disadvantages this simple embodiment is operative.

Figure 4:
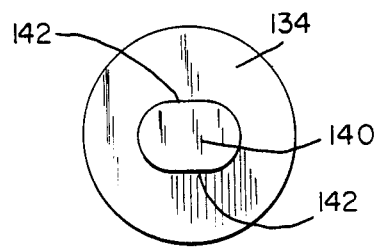
FIG. 4 is an axial cross-sectional view of the embodiment of FIG. 1 viewed from 4—4 showing a particular improvement thereon.

The preferred embodiment of the invention is that illustrated in FIG. 1 with the improvement illustrated in FIG. 4.

This embodiment comprises, in the frozen state, a rectal insert 100 having a substantially cylindrical portion 110 provided with a substantially conical nose portion 112. Rearwardly of section 110 is provided a collar section 114 which, most desirably, is provided with a substantially frustro conical cross-sectioned forward face 114 to facilitate passage of the collar thru the sphincter muscle and a rearward face 118 to reduce the likelihood of the device, once inserted, being expelled outwardly through the sphincter. Rearwardly of collar 116 is substantially cylindrical mid-section 120. Rearward of this section 120 is provided a rearward collar 130 having a forward buffer face 132 and a rearward face 134. It is not essential that collar 130 entirely girdle the device since its sole purpose is to act as a stopper preventing the passage of the entire device through the sphincter muscle. Nevertheless, it is both simple to provide for 130 to entirely girdle the device and furthermore, such construction substantially strengthens collar 130.

Rearward of stopper 130 is holding section 140. The presence of this additional section is a matter of mere convenience and is in no way essential to the operation of the device. Numerous conveniences can be incorporated thereon, if desired, for example, as illustrated in FIG. 4, two of the sides of 140 can be shaved to the substantially mutually parallel arrangements 142 illustrated which would make it easier to hold the device between two fingers when inserting the same or removing the same. Similarly, a holding means of cloth, plastic, wood, or other materials may be incorporated into sector 140 and protruding therefrom to provide a drier surface for handling during insertion or removal. Again these are a matter of convenience and do not affect the essential operation of the device. It is contemplated that after insertion the frozen hydrogel will melt, thus reducing the external dimensions of the device including but not limited to, forward collar 116 to the point at which the device will either to auto-expelled by the sphincter muscle when the subject is in the sitting position or the dimensions will be so reduced that the device can readily be withdrawn outwardly through the sphincter muscle.

Nevertheless, there are circumstances wherein it would be desirable to maintain the entire segment of the insert forward of sector 120 inside the rectum and, after substantial completion of the cooling effect be permitted to travel up the colon in the manner of a conventional suppository.

Figure 6:
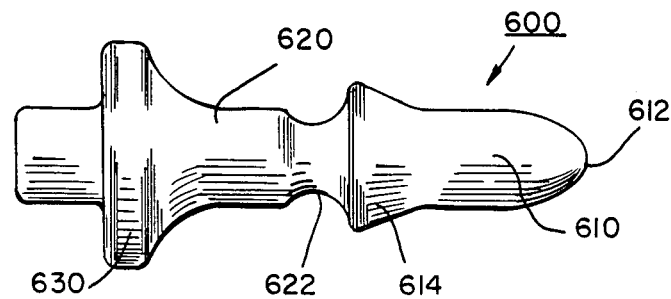
FIG. 6 is another embodiment of the rectal insert of the present invention especially suited for the use thereof for drug delivery.

This embodiment is particularly preferred when the treatment calls for the additional delivery of a pharmaceutically acceptable amount of a rectally administrable pharmaceutically active compound. One form of this embodiment is illustrated in FIG. 6 which has some of the characteristics of FIG. 1 device and some of those of FIG. 5 device. Particularly to be noted, however, in device 600 of FIG. 6 is a very substantial narrowing of mid-section 620 so that its diameter is between 25 and 75% that of, say, forward shaft portion 110. Needless to say the sphincter will rest within this indentation and exert excess pressure thereon to the point at which this segment will melt and break prior to the melting of the forward segments of the insert causing the insert to be propelled up into the colon as mentioned hereinbefore.

In an unillustrated modification of this embodiment forward collar 614 is omitted.

Figure 2:
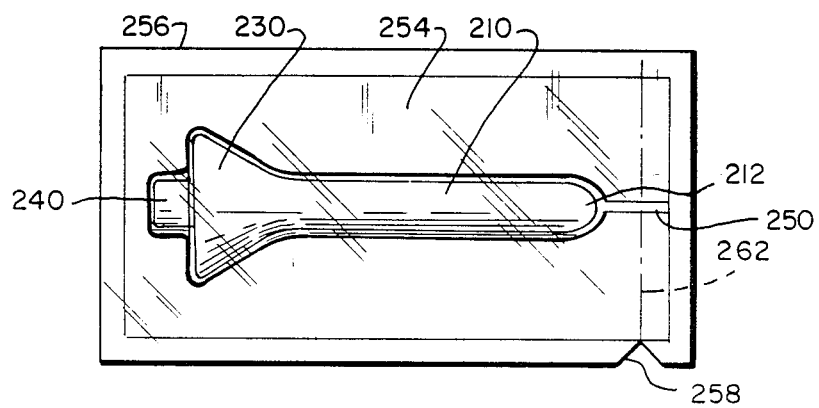
FIG. 2 is a plan view of a package for another embodiment of the present invention.
Figure 3:
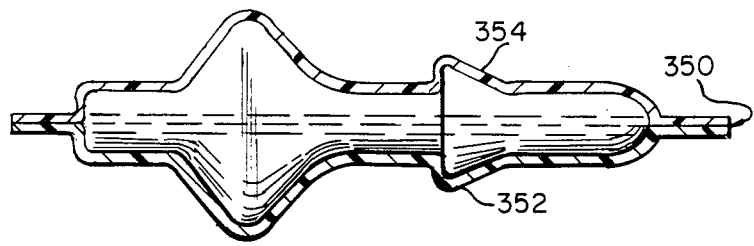
FIG. 3 is a side cross-sectional elevational view of a package for the embodiment of FIG. 1.

As mentioned heretofore at ambient temperatures the device may be in a gel form which is not or substantially not self retentive of form. Since it is convenient to package it in this manner and it is unnecessary to maintain a device in the frozen state except just prior to use, it is convenient to employ any disposable type of blister packaging. It is, however, particularly advantageous to utilize heat formable sheets of thermo plastic material. One modification of such packaging is illustrated in FIGS. 2 and 3. The packaging 256 comprises a pair of pre-shaped blister sheets 254 and (not illustrated) 252. These are sealed around the edges thereof by thermal bead seal 256. In manufacture of the device the gel material is injected into space 210 by conventional means through orifice 250 after which the seal is completed.

In order to facilitate opening of the package there may, optionally, be provided assisting means such as notch 254 and score line 262. It will be noted that as described above, the flat portion of package 256 is only sealed together at the edge. While such otherwise unsealed contact is not an essential part of the invention and these flat portions may be sealed together, for example, by heat sealing, leaving them unsealed substantially facilitates opening of the device. Thus, it will be clear to those skilled in the art that the actual location of the heat seal 256 although illustrated as a circumferential bead seal may be located at other places on the packaging as long as it is circumferential to the location of the gel matter itself. Indeed as mentioned above where "soft" packaging is employed for a gel in substantially fluid form at ambient temperature, the circumferential seal should actually outline the shape of the insert.

Figure 7:
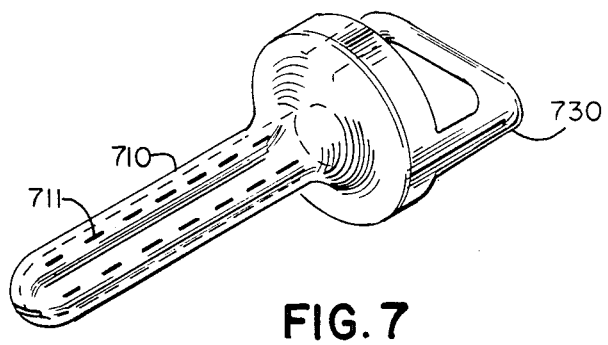
FIG. 7 is a perspective plan view of an embodiment of a present invention comprising a handle and collapsible insert filled with hydrogel.

The embodiment of FIG. 7 comprises a handle portion 730 and a tubular portion 710 having a multiplicity of orifices 711 therein. The aforesaid combined article comprising segments 710 and 730 may be made of any soft collapsible material including but not limited to multiblock co-polymer hydrogel of acrylonitrile and acrylamide having an equilibrium swelling of 73% with water. Such a hydrogel polymer is recommended because of cheapness but other polymers or rubbers may also be employed.

This portion of the device is placed in a mold similar to that depicted in FIGS. 2 and 3 and the hydrogel suitably a hydrogel comprising more than 90% by weight of water is injected into the mold so that entire section 710 is filled therewith. After freezing in the usual manner, the device is inserted in the usual manner.

While the device of this embodiment may either be used in the subject face down position or else hand held for a subject in the sitting position, the form of the handle will tend to eliminate many of the esthetic problems of, say, the device of FIG. 5. As the inserted portion of the device becomes warmer the combination of melting and pressure of the rectal muscles will force the gel out of the orifices 711 and, after a predetermined time, the device can be withdrawn and discarded. This particularly form of device is well suited for the contemporaneous administration of pharmacologically active agents which are to be administered rectally, and due to its design there is no possibility that an attempt would be made to recharge or re-use the remaining carrier portion after one employment.

Figure 8:
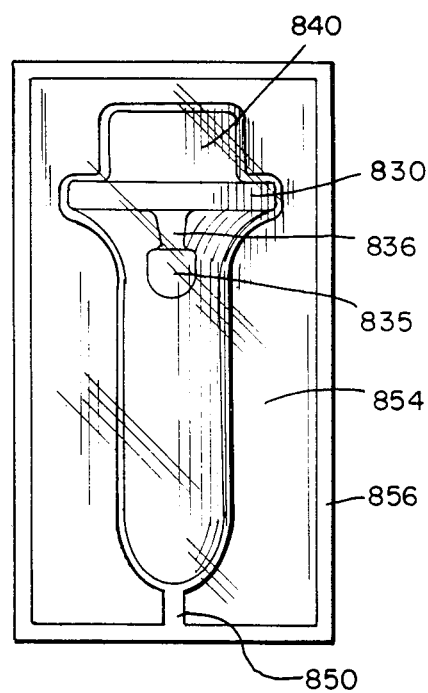
FIG. 8 is a plan view of a package comprising yet another embodiment of the invention wherein the insert portion comprises the hydrogel segment and a substantially rigid combined carrier and blocking portion therefore.

FIG. 8 illustrates yet another embodiment of the invention wherein the handling portion and the rearward collar portion are made of materials other than hydrogel. In this embodiment the package comprises the usual blister pack 854/852 sealed by circumferential heat seal 856. Within the bubble there is provided a rearward portion comprising the handle segment 840 and the rearward collar section 830. For reasons of stability in use, a longitudinal protrusion 836 having a small bar or plug 835 attached thereto perpendicular to the longitudinal axis, serves to avoid the premature separation of the gel portion of the insert from the handle portion.

The hydrogel is introduced through orifice 850 in pack 854 which is subsequently sealed in the conventional manner.

While the embodiment of FIG. 8 does not illustrate a forward collar such as that shown as item 114 in FIG. 1, such a forward collar could readily be incorporated but would, suitably, be of frozen hydrogel. The insert of FIG. 8 is utilized in a similar manner to that of FIGS. 2, 5 and 7. The use of a non-hydrogel handle and rearward collar is more desirable esthetically but tends to raise the cost of the insert not only because of the cost of the materials involved but because of the necessity of several additional manufacturing steps including but not limiting to the actual manufacture of the handle portion and its insertion into the package prior to the injection of the hydrogel.

The hydrogel rectal insertion of the present invention comprises (a) an essentially cylindrical stem of diameter about 5 to 15 mm and of length 35 to 125 mm, made of hydrogel having equilibrium water content higher than about 35% preferably over 90% most suitably 95-99% by weight and a substantial part of the swelling water freezing between −1 and +1 deg. C., which stem is to be inserted into the rectum in frozen state; and desirably, (b) a non-insertable end which adheres firmly to the said stem at least in its frozen state. While this non-insertable end may, as described above, comprise a hydrogel collar, the invention is not so limited and it may be made of any rigid material such as wood, plastic or cardboard.

The hydrogel mentioned above is a crosslinked or non-crosslinked polymer which swells in water to a certain equilibrium water content but is water-insoluble at ambient or body temperature. The equilibrium water content at ambient temperature is at least 35% by weight, based on swollen hydrogel; and a substantial part of the swelling water is in a free state, being crystallizable in the same manner as water itself. Thus, an essential feature of the hydrogel used in present invention is its content of water in two states—hydration water (which does not freeze) and free water freezes close to 0° C. The hydrogels usable in our invention contain a substantial proportion of water crystallizable at near sub-zero temperatures, while the remaining part of the water serves to hydrates the polymer molecule. (for more details on free, or mobile, and bound water phases in hydrogels see e.g. Andronikashvili et al,: Biopolymers, 1976, 15, 1991).

The mobile water phase has the following major funtions: it contributes substantially to heat capacity of the system and it assures that temperature of the molten outer layer of hydrogel is close to, but not below 0° C.

The bound water plasticizes the polymer which would otherwise be brittle (mixture of ice crystals and non-plasticized polymer would be as brittle as or even more brittle than ice itself).

Although certain hydrogels can have as little as 35% of swelling water to be useful in the present invention, the hydrogels with water content over 70% of water are preferred. At this water content the mobile water distinctly prevails over the bound water even if the gel is homogeneous. The mobile water consists of cage-like structures which cannot be fully developed if the pores or intermolecular spaces are smaller than about 40 to 50 °A. The percentage of such small spaces decreases with swelling capacity, and at about 70% of water the volume of the large pores prevails even for hydrogels with large inherent binding capacity.

We have found that the freezing characteristics of some hydrogels with swelling capacity between 35 and about 70% of water depend, to some extent, on conditions of their preparation, thermal history, etc. The hydrogels with higher water content than about 70% are, on the other hand, only very slightly sensitive to those factors. Moreover, both heat capacity and thermal conductivity increase with increasing water content at a substantially exponential rather than linear rate, and above about 70% of water the contribution of the mobile water to the thermodynamic characteristics starts to prevail over the contributions of the bound water and the polymer in readily predictable way.

Basically any polymer swelling capacity of over 70% of water can be used in the present invention. Examples of such polymers are polymers and copolymers of acrylamide, methacrylamide, and their N-substituted derivatives; polymers and copolymers of acrylic, methacrylic, maleic and itaconic acids; polymers and copolymers of hydrophilic esters of acrylic and methacrylic acid, such as 2-hydroxyethylmethacrylate, glycerylacrylate and similarly; polymers and copolymers of vinyl pyrridine, or vinylpyrrolidone; polycondensates of polyethers, such as poly(ethylene) or poly(propylene)-glycos and their graft or block copolymers; polysaccharides, such as starch; cellulose and its derivatives, such as methylcellulose; polypeptides, such as collagen or elastin or gelatin; and mixtures containing a substantial portion of such hydrophilic polymers.

The said hydrogels can be covalently cross-linked in the manner well known per se, e.g. by copolymerization with bifunctional copolymers, by aldehydes or by irradiation, depending on the polymer type.

The non-crosslinked, though water-insoluble hydrogels are preferred because of their better processing characteristics in general.

Particularly preferred hydrogels are those derived from poly(acrylonitrile) and containing amidic and/or carboxylic functional groups. There are several classes of such hydrogels. One of them contains block copolymers of acrylonitrile, as described e.g. in U.S. Pat. No. 4,337,327.

The other class are acrylonitrile-grafted and subsequently hydrolyzed polysacharides, such as starch. This type of hydrogels has been described in numerous papers, such as M. O. Weaver et al., Journal of Applied Polymer Science, Vol. 15, pp. 3015-3024 (1971). Similar copolymers can be prepared by direct grafting of acrylamide onto starch, as described e.g. by G. F. Fanta et al., Journal of Applied Polymer Science Vol. 16, 2835-2845 (1972). The above mentioned hydrogels can form hydrogels with very low content of solids and with very high content of freezable water. The hydrogels are very soft in the molten state and they have lubricating properties.

We found it advantageous if a major part of the insert is formed from a hydrogel with water content higher than 90% and preferably higher than 98% of water which has following properties:

(1) it is strong enough in molten state between 0° and 50° C. to retain its integrity in a plastic wrapping foil, but it disintegrates under the pressure of the sphincter muscle, when molten, to a lubricating jelly;

(2) its swelling capacity in water strongly increases with temperature;

(3) it can be molten in presence of water at a temperature between about 50° and 105° C. Examples of such hydrogels are multiblock copolymers of acrylonitrile-acrylamide with water content between about 95 and 99.7% of water; gelatine with water; starch gels; and the mixtures thereof.

There are several advantages of the use of the high-water content hydrogel collapsible by pressure. Firstly, the collapsible hydrogel forms a lubricating (molten) layer on the surface of the frozen insert. Secondly, the collapse of the hydrogel by melting in rectum prevents its re-use on the one hand, and provides a protective and lubricating layer on the rectal tissue on the other.

Thirdly, the collapse of the molten layer improves heat transfer between the tissue and the frozen core of the insert. Both the tissues and the core have roughly constant temperature and the collapse of the hydrogel ensures that the heat transfer is mediated by a hydrogel layer of constant heat conductivity and of constant thickness.

The increasing swelling capacity with temperature causes expulsion of certain amount of free water during the melting. The water and the excess of molten and disintegrated hydrogel are expulsed from rectal channel into the bottom of the colon, helping to soften excrements and protect the rectal tissue at stool.

The additional advantage of the collapsible hydrogels is that they stay in the rectum much longer than the insert itself. The cooling function of the insert lasts several minutes, while the lubricating and medicating function of hemorrhoidal suppositories has to last much longer to be effective. Hence, the use of the collapsible hydrogel enables us to combine functions of the cooling insert, suppository and ointment in single device.

While it is the principal purpose of the present invention to provide for the shrinking of hemorrhoids by reducing the temperature of their environment, it is within the scope of the present invention to utilize the devices disclosed and claimed herein as drug delivery systems both as an additional treatment for hemorrhoids or for any other desirable physiological effect in which there is incorporated in the rectal insert a desired pharmaceutically acceptable amount of any predetermined rectally administerable pharmaceutically active compound.

When administered the medication can be either dissolved in the water phase or dispersed in the hydrogel, depending on its solubility in water. Particularly useful are drugs causing symptomatic relief of inflamation and swelling such as Dexamethasone, Hydrocortisone, Phenylbutazone or Prednisolone; local anesthetics, such as Phenazopyridine or Procaine; tissue-shrinking drugs, such as Phenylpropanol amine; antibiotics; natural substances used in hemorroidal ointments or suppositories, such as shark-liver oil, yiest cell derivatives and the like.

The water-insoluble substances can be dissolved in oily substances (e.g. regular rectal ointment bases) which are subsequently dispersed in the hydrogel. As long as a major part of hydrogel is used so that the dispersion is of oil-in-water type, the oily substances do not interfere with the freezing process. On the other hand, they further improve lubrication and the transport of the drugs into the tissue. The amount of medication then administered both with respect to concentration and dosage amount is substantially similar to that employed in conventional suppositories using those medicaments (see Physicians Desk Reference, U.S. Pharmacopoea etc.).

EXAMPLES

Example 1

40 weight parts (w/w) of 2-hydroxyethyl methacrylate monomer containing 0.7% of ethyleneglycol dimethacrylate was mixed with 60 parts (w/w) of water and 0.5 parts (w/w) of 30% hydrogen peroxide. The mixture was polymerized at 65° C. in a polyethylene mold. After the polymerization was finished, the mold was opened and the polymerized article was washed thoroughly with water. The spongy hydrogel in the form depicted in FIG. 5, having insertable stem 510 with rounded tip 512, and the enlarged non-insertable end portion 530, was packaged in heat-contractable plastic foil. The hydrogel itself contained 60% of water, of which about 20% of freezable water was contained in the microscopic pores.

Example 2

Multiblock copolymer hydrogel consisting of acrylonitrile and acrylamide, having an equilibrium swelling 73% of water, was injection-molded into a hollow tubular article 710 with multiple orifices 711 and end handle-like portion 732 as depicted in FIG. 7.

1 part (w/w) of powdered copolymer of starch grafted with acrylonitrile and subsequently hydrolyzed by sodium hydroxide), was washed, dried and mixed with 5 parts of (w/w) of potato starch and with 100 parts (w/w) of water. The paste was heated to 100° C. to liquify it.

The cavity 713 of the hydrogel article 710 was then filled with the hot liquified paste, which was subsequently gelified by cooling.

The outer wall 715 of the hydrogel article 710 having a water content of 73% has lower thermal conductivity than the hydrogel with high water content inside, thus prolonging the cooling action. It simultaneously protects the weak gel inside during transport and handling. The molten gel inside the device is disintegrated by rectal pressure and squeezed out of the jacket by the side and end orifices. The outer hydrogel jacket is extracted from the anus after the inner gel becomes molten and is left behind as lubricant and, potentially, as a drug carrier.

Example 3

Polyacrylonitrile of molecular weight 350,000 was dissolved in mixture of 71% nitric acid and 98% sulfuric acid (9:1 w/w) to form a viscous solution having 5% of solids (w/w). The solution was allowed to stand for 240 hours so that the nitrile groups were substantially all hydrolyzed, then the solution was poured into excess of cool water so that the polyacrylonitrile hydrolyzate (PAN) coagulated. The clear soft gel with equilibrium swelling over 95% of water was thoroughly washed, dried and ground to a fine powder.

7.5 parts (w/w) of the powdered PAN hydrolyzate was added to 990 parts (w/w) of water and heated to boiling point until the powder dissolved. The solution thus formed was gellified by cooling to ambient temperature to a clear, soft gel which could be disintegrated by a moderate pressure.

The two part mold is prepared from PVC foil 0.0075" thick as depicted in FIG. 3.

The parts 352 and 354 are assembled and their inner cavity filled by the hot solution described above by injection thru inlet 350 (not illustrated, but similar inlet 250 in FIG. 2. The solution was cooled down in water bath and the injection inlet The resulting article comprising the PVC jacket (divisible to part 352 and part 354) and the soft hydrogel inside are cooled to a $-15°$ C. before use. After the hydrogel is frozen, the insert may be dipped briefly into warm water so that a thin layer of gel beneath the PVC jacket melts. The parts 352 and 354 are separated and the insert inserted into the rectum of the patient.

Example 4

5 parts of rectal ointment, containing 3% of Liver Shark Oil; Live Yeist Cell Derivative, supplying 2000 units Skin Respiratory Factor per ounce of the ointment; and 0.01% of Phenylmercuric nitrate (Preparation H. Whitehall Laboratories Inc., N. York) were finely dispersed in 95 parts of the hot aqueous polymer solution from Example 3. The hot dispersion was filled into the two-part mold/container from the Example 3 where it gelled to solid dispersion.

EXAMPLE 5

1 part of procaine hydrochloride and 1 part of phenylbutazone were dissolved in 98 parts of 1% aqueous polymer solution (the polymer is the powerdered polymer described in the Example 3). The hot solution was injected into the mold/container 854 thru inlet 850, so that the whole space 810 between the collar 830 and the PVC foil container was filled by the medicated hydrogel. Then the container was closed by welding inlet 850.

We claim:

1. A package means for treatment of rectal disorder comprising
    a disposable substantially form retaining package of predetermined shape enveloping a water swellable polymer in gel form comprising at least 35% by weight of water, said gel being selected to provide an insert of sufficient rigidity to be inserted into the rectum after said insert has been cooled to below 0° C.
    said insert, when frozen, comprising a substantially cylindrical body provided with a substantially conical nose at one end thereof and a rearward collar proximate to the other end thereof, said nose facilitating insertion and said collar preventing initial total passage of the insert beyond the sphincter muscle of the rectum.

2. A package means in accordance with claim 1 additionally comprising a forward collar section located upon the cyclindrical body rearwardly of the nose section and forwardly of the real collar, the forward face of said forward collar section having a substantially frustro-conical cross-section and the rearward face of said forward collar section lying in a plane substantially perpendicular to the longitudinal axis of the insert, whereby there is provided a substantially cylindrical midsection between the rearward face of the forward collar and the forward face of said rear collar.

3. A package means in accordance with claim 1 wherein the rearward collar is displaced a sufficient distance forward of the rear end of the insert to enable the remaining rear portion to be finger held.

4. A package means in accordance with claim 3 wherein at least one portion of the curved surface of said rear most section is flattened to lie substantially in a plane substantially parallel to the longitudinal axis of the insert.

5. A package means in accordance with claim 2 wherein at least a portion of said mid-section has a diameter less than the maximum diameter of the nose section of the insert.

6. A device in accordance with claim 5 wherein said mid-section has a diameter of between 50 and 25% of the maximum diameter of the nose section.

7. A package means in accordance with claim 2 wherein the diameter of the forward collar is between 150% and 250% of the maximum diameter of the nose section.

8. A package means in accordance with claim 1 wherein the gel comprises at least 90% water.

9. A package means in accordance with claim 7 wherein the gel comprises at least 98% by weight of water.

10. A package means in accordance with claim 8 wherein the device comprises a multi block copolymer of acrylonitrile acrylamide having a water content of between 95 and 99.7% by weight.

11. A package means in accordance with claim 1 additionally comprising a pharmaceutically acceptable amount of a rectally administrable pharmaceutically active compound.

12. A method of treating hemorrhoids which comprises inserting into the rectum of a subject afflicted therewith a substantially cylindrical insert shaped and dimensioned to enter readily thru the rectal sphincter muscle, said insert comprising a water swellable polymer having a water content of at least 35% by weight, said insert having previously been frozen by being subjected to a temperature below 0° C. for a sufficient amount of time to freeze the free water therein and maintaining said insert with at least a portion thereof outside the sphincter muscle for at least one minute.

13. A method of claim 12 which comprises inserting into the rectum of the subject affected by hemorrhoids a substantially cylindrical device having a substantially conical nose end for insertion and a collar means having a diameter substantially greater than the maximum diameter of the nose portion located proximate to the rear end of the insert to prevent the passage of the entire insert through the sphincter muscle.

14. A method in accordance with claim 12 wherein the device comprises at least 90% by weight of water.

15. A method in accordance with claim 14 wherein the insert comprises at least 98% by weight of water.

16. A method in accordance with claim 12 wherein the insert comprises a multiblock copolymer of acrylonitrile acrylamide having a water content of 95 to 99.7% of water.

* * * * *